United States Patent [19]

Thomas

[11] 4,248,227

[45] Feb. 3, 1981

[54] FLUID UNIT DISPENSING DEVICE

[75] Inventor: Ralph H. Thomas, Clark, N.J.

[73] Assignee: Bristol-Myers Company, New York, N.Y.

[21] Appl. No.: 38,989

[22] Filed: May 14, 1979

[51] Int. Cl.$^{3}$ .................... A61M 1/00

[52] U.S. Cl. .................... 128/232; 128/261; 222/541

[58] Field of Search .................... 128/232, 260, 231, 272, 128/261, 271, 213 R; 222/92, 541

[56] References Cited

U.S. PATENT DOCUMENTS

| | | | |
|---|---|---|---|
| 1,699,965 | 1/1929 | Herzog | 128/232 |
| 2,857,914 | 10/1958 | Carliner | 128/232 |
| 3,128,920 | 4/1964 | Volckening et al. | 128/232 X |
| 3,777,949 | 12/1973 | Arias | 222/541 |
| 3,785,366 | 1/1974 | Davis | 128/232 X |
| 4,052,986 | 10/1977 | Scaife | 128/260 |

*Primary Examiner*—John D. Yasko
*Attorney, Agent, or Firm*—Irving Holtzman; George A. Mentis

[57] ABSTRACT

A flexible unit dispensing device for a fluid comprising a squeezable hollow bulb portion and a cylindrical nozzle. The internal diameter of the nozzle is no smaller than 0.120 inches and the length of nozzle being such as to reach to the area of the rectal columns when the device is inserted in the anal canal.

4 Claims, 6 Drawing Figures

FLUID UNIT DISPENSING DEVICE

This invention relates to a dispensing package suitable for delivering a fluid product into the anal canal. This is useful in, but not restricted to, the delivery of therapeutic liquids or creams for the treatment of hemorrhoids.

In the treatment of hemorrhoids, the regimen often calls for the self-administration of liquids or creams into the anal canal. This has presented several problems. In the first place, self-access to the anal canal is difficult, making it a problem to conveniently apply sufficient pressure to the dispenser so that it can be adequately emptied and deliver to the affected area the required amount of medicament. Secondly, the proper therapeutic treatment often times calls for the deposition of the medicament at the appropriate level in the anal canal; that is, at the level of the affected hemorroidal tissue. Thirdly, since the tissue under these conditions is often inflamed and painful, it is necessary to deliver the medicament with a minimum of manipulation.

It has now been found that the above described problems can be handled by providing a unit dosage dispenser in the form of a squeezable or flexible bulb having a nozzle of sufficient length to reach the affected areas in most cases of hemorrhoids and of such dimension as to make the delivery of the medicament possible with the application of a minimum of pressure and to make the insertion possible with a minimum of discomfort.

It is accordingly an object of the present invention to provide a unit dosage dispenser having the characteristics described above.

Other and more detailed objects of this invention will be apparent from the following description, claims and drawings wherein:

Figure 1:
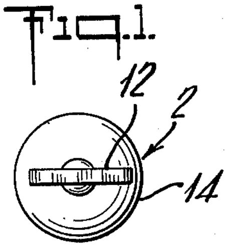
FIG. 1 is a top plan view of a dispenser embodying the present invention.
Figure 3:
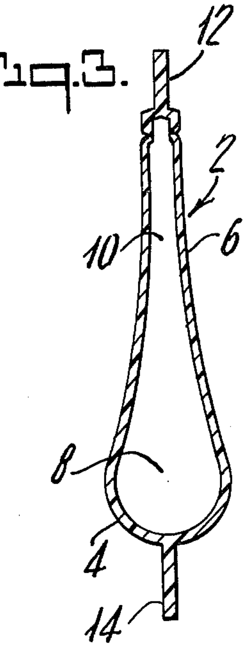
FIG. 3 is a longitudinal cross-sectional view of the dispenser of FIG. 2 taken along line 3—3′.
Figure 2:
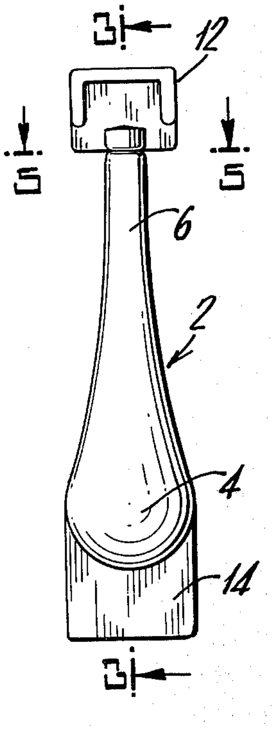
FIG. 2 is a front elevation of the dispenser of FIG. 1, the back elevation having the same configuration.
Figure 5:
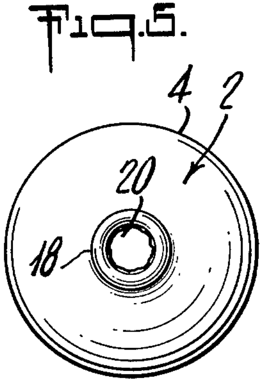
FIG. 5 is an end elevation of the dispenser of FIG. 2 in which the sealing element has been broken off along line 5—5′.
Figure 4:
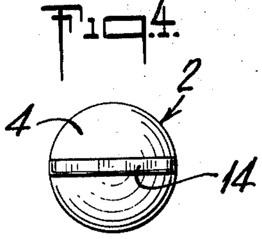
FIG. 4 is a bottom plan view of the dispenser of FIG. 1.

Referring now to the drawings in which the same number designates the same structure in the various views, a dispenser embodied in the present invention is shown generally at 2 and comprises a bulb portion 4 and a nozzle 6. Bulb portion 4 on its interior comprises a hollow single chamber 8 which tapers gently to form a cylindrical nozzle canal 10. As will be seen by a comparison of FIGS. 2 and 3, the external configuration of bulb portion 4 and nozzle 6 follow generally the shape of bulb chamber 8 and nozzle canal 10.

Removably secured to the end of nozzle 6 there is provided a break-off tab 12 which serves to seal off the end of nozzle canal 10. Break-off tab 12 is preferably secured to the end of nozzle 6 so that it may be readily removed by a twisting motion.

Bulk portion 4 of dispenser 2 is provided with a finger tab 14. This serves to facilitate the handling of the dispenser when it is to be inserted into the anal canal.

It is a feature of the present invention to minimize the discomfort that the user of this device may encounter. When the break-off tab 12 is removed, there is the potential that rough edges may remain at the nozzle end which would tend to cause pain when the dispenser is inserted into the anal canal.

Figure 6:
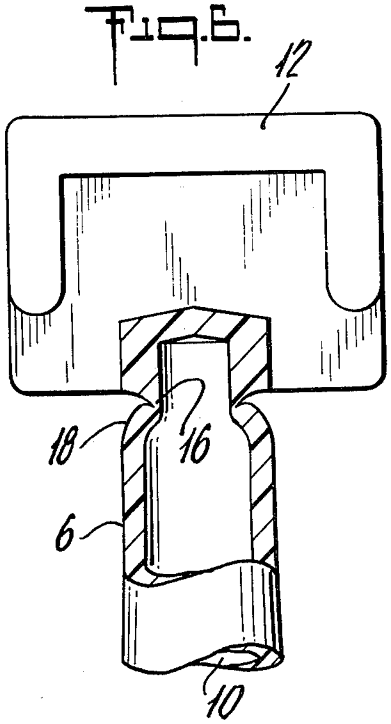
FIG. 6 is an enlarged detailed view partially in section of the relationship of the break-off tab to the end of the dispenser nozzle, the break-off tab being shown in position within the nozzle end.

To avoid this, a construction is employed which is best illustrated in the enlarged detailed view shown in FIG. 6. As will be seen in this drawing, the upper margin of nozzle 6 is rounded off to provide a smooth curved surface 18 that extends down into the nozzle orifice 20. In addition, the bottom portion of break-off tab 12 is provided with a step 16 which is joined to nozzle 6 inside nozzle orifice 20. As a consequence, when break-off tab 12 is removed from the nozzle 6 as by a twisting motion, the roughened fracture line is within the nozzle orifice and out of any position which might tend to irritate the tissue when the dispenser is inserted into the anal canal.

The dispensing device of the present invention containing product can be formed in several ways. One procedure involves first forming by way of blow molding technique, a semi-finished unit in which the break-off tab 12, nozzle 6, and an open-ended tubular portion are molded as a unit. This semi-finished piece is then loaded through the bottom with, for example, the medicated cream and sent on to a forming and sealing station at which the formation of bulb 4 is completed, finger tab 14 is formed and the device is sealed. This is accomplished with material from the tubular portion of the semi-finished unit.

In a second procedure, an upper tubular section, bulb portion 4 and finger tab 14 are blow molded as a single unit. The medicated cream is then loaded into the device through the upper tubular opening. In a manner similar to the prior procedure, break-off tab 12 and nozzle 6 are formed and the device is sealed in a single forming and sealing step using material from the upper tubular section.

The present dispenser is inteded to take the form of a squeezable or flexible device. Any of a variety of materials may be used in molding this dispenser to get these characteristics. However, in the preferred form of the invention, the dispenser is molded of low density polyethylene.

As previously indicated, certain dimensional parameters of the present dispensing device are essential for obtaining a dispensing device that will deliver medication conveniently to the affected hemorrhoidal tissue at a minimal pressure and with a minimum of discomfort. One of such parameters is the internal diameter of the discharge orifice of the nozzle after the break-off tab has been removed. It has been found that to accomplish the present purposes, this diameter should not be smaller than about 0.120 inches. This controls the discharge pressure and gives an adequate product flow rate.

A second critical dimensional parameter is the length of the cylindrical tapered nozzle 6. This needs to be long enough to pass through the internal sphincter muscles of the anal canal and into the area of the rectal columns which are usually swollen and inflamed when the subject is suffering from hemorrhoids. It has been found that the appropriate length of the tapered nozzle to deliver the medicated material to the appropriate place is about 1⅝ inches.

The bulb portion 4 of the dispenser has to be fashioned with two thoughts in mind. It needs to be designed to act as the external sphincter muscles so as to prevent total entry of the device into the anal canal. Secondly, it needs to provide an adequate pressing area for the thumb and forefinger for dispensing the product into the hemorrhoidal region. It has been found that a bulb having a greatest diameter of about at least 0.750 inches very adequately serves the present purposes.

The outside diameter of the nozzle 6 is controlled to provide the smallest device which can be comfortably inserted into the anal canal and at the same time, allow for good distribution and coating of the medicated product on the rectal columns. This may vary somewhat but a suitable diameter is 0.240 inches.

The height of step 16 is also selected to insure that any rough edges remaining on nozzle 6 resulting from the removal of the break-off tab 12 are inside the neck of nozzle 6 and not outside where they could cause irritation. A step height of about 0.030 inches has been found to be quite suitable.

Break-off tab 12 is designed to provide an adequate area for gripping it with the forefinger and thumb so that an adequate force can be applied to break off this tab. In a preferred form of this invention, the width (i.e. the horizontal dimension) is about 0.625 inches; whereas, the height (i.e. the vertical dimension) is 0.500 inches.

Finger tab 14 is designed for ease of handling of the dispenser when it is being self-administered. Its dimensions can vary somewhat. A finger tab that has a vertical dimension of 0.500 inches and a horizontal dimension of 0.750 inches has been found to be quite adequate.

The overall dimensions of the present dispenser i.e. its maximum vertical dimension and its maximum horizontal dimension may also vary somewhat. Ordinarily, it will be designed to hold about 5 grams of product so as to assure a delivery of at least 3 grams of product to the affected area. A device that had an overall vertical dimension of 3.625 inches and a horizontal dimension of 0.750 inches has been found to be quite suitable.

To allow for machine filling and to provide a delivery of a minimum of 3 grams of product, the product is introduced into the dispenser to a level of about 2.187 inches from the bottom of the bulb chamber. Although this can vary somewhat, this has proven to be a very convenient level.

Although the invention has been described with reference to specific forms thereof, it will be understood that many changes and modifications may be made without departing from the spirit of this invention.

What is claimed is:

1. As an article of manufacture a sealed, flexible unit dosage dispensing device containing a fluid product, said device comprising a squeezable hollow bulb portion and a generally hollow cylindrical nozzle portion communicating internally with said hollow bulb portion and provided with a nozzle orifice; the internal diameter of said nozzle portion being no smaller than 0.120 inches, the length of said nozzle portion being 1⅝ inches thereby being sufficient to reach at about least, and substantially no further than about the area of the rectal columns when inserted into the anal canal of a subject; the largest diameter of said hollow bulb portion being 0.750 inches thereby being sufficiently large to serve as a stop to prevent the insertion of the device too deeply into the anal canal; the terminal portion of said nozzle portion being rounded off to provide a smooth surface that extends down into the nozzle orifice; said dispenser being provided with a break-off tab to seal the terminal end of said nozzle, said tab being adapted to be removed from said nozzle to expose a terminal nozzle orifice whereby the contents of said dispenser can be dispensed through said orifice by squeezing said bulb portion; said break-off tab being provided with a step extending downwardly from the undersurface of said break-off tab, the outside diameter of said step being such that it fits into the terminal end of said nozzle portion; said step being joined to said nozzle inside said nozzle orifice whereby when said break-off tab is removed from said nozzle by a twisting motion, the roughened fracture line is within the nozzle orifice and out of any position which might tend to irritate the tissue when the dispenser is inserted into the anal canal.

2. A dispensing device according to claim 1 including a finger tab secured to and extending downwardly from the bottom of said bulb portion, said finger tab serving to facilitate the handling of said dispenser during its insertion into the anal canal.

3. A dispensing device according to claim 2 in which the outside diameter of said nozzle portion is 0.240 inches.

4. A dispensing device according to claim 3 in which said step has a height of 0.030 inches.

* * * * *